Figure 1:
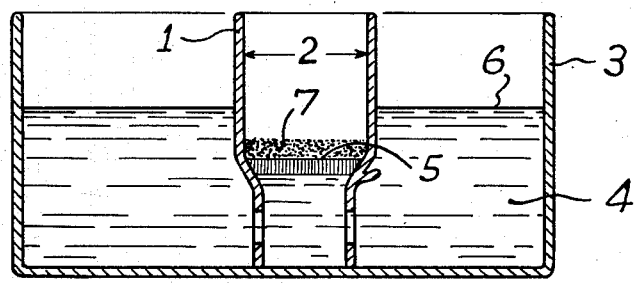

United States Patent [19]

Grouiller

[11] 4,340,699
[45] Jul. 20, 1982

[54] PROCESS FOR PREPARING A POLYMER OF THREE-DIMENSIONAL STRUCTURE OF THE CROSS-LINKED POLYURETHANE TYPE, PRODUCT OBTAINED ACCORDING TO THIS PROCESS AND APPLICATION THEREOF AS SWELLING AGENT, PARTICULARLY IN THERAPEUTICS

[75] Inventor: Hervé Grouiller, Chenove, France

[73] Assignee: Laboratories d'Hygiene et de Dietetique (L.H.D.), Paris, France

[21] Appl. No.: 278,845

[22] Filed: Jun. 29, 1981

[30] Foreign Application Priority Data

Jun. 30, 1980 [FR] France .................. 80 14515

[51] Int. Cl.³ .............................................. C08G 18/30
[52] U.S. Cl. .................. 525/460; 525/453; 528/73
[58] Field of Search ............... 525/460, 453; 528/73

[56] References Cited

U.S. PATENT DOCUMENTS 4,000,214 12/1976 Lum et al. ............................ 525/453
4,127,516 11/1978 Larsen et al. ....................... 521/137
4,143,009  3/1979 Dewey ................................. 528/73

FOREIGN PATENT DOCUMENTS 2130202 11/1972 France .

Primary Examiner—Maurice J. Welsh
Attorney, Agent, or Firm—Schwartz, Jeffery, Schwaab, Mack, Blumenthal & Koch

[57] ABSTRACT

The present invention relates to a process for preparing a polymer of the cross-linked polyurethane type, whereby (1) the following are reacted:
 (a) a polyolether, chosen from the group constituted by the oxyalkylene polyols (I) and mixtures thereof, obtained by condensation of a polyol (II) containing at least 2 OH groups and preferably 3 to 6 OH groups with an alkylene oxide (III) at a rate of 1 to 20 moles of (III) per free OH group of (II), and
 (b) a polyisocyanate (IV),
the reaction being effected with an excess of OH groups of (I) with respect to the NCO isocyanate groups of (IV) to obtain a polyurethane-polyol (V) having free OH groups; and
(2) the polyurethane-polyol (V) thus obtained is reacted with epichlorhydrin (VI) and a polyamine (VII) chosen from the polyamines having at least two $NH_2$ amino groups and mixtures thereof. The invention also relates to this polymer as new industrial product and to its application as swelling agent.

20 Claims, 4 Drawing Figures

U.S. Patent   Jul. 20, 1982   Sheet 1 of 2   4,340,699

PROCESS FOR PREPARING A POLYMER OF THREE-DIMENSIONAL STRUCTURE OF THE CROSS-LINKED POLYURETHANE TYPE, PRODUCT OBTAINED ACCORDING TO THIS PROCESS AND APPLICATION THEREOF AS SWELLING AGENT, PARTICULARLY IN THERAPEUTICS

The present invention relates to a process for the preparation of a polymer of three-dimensional structure of the cross-linked polyurethane type. It also relates to the polymer obtained according to this process, both as new industrial product and its application as swelling agent useful in particular in therapeutics, particularly as anorexiant agent, lipid-lowering drug and agent sequestering biliary acids.

Macromolecular substances of three-dimensional structure having a swelling power and useful in particular as ion exchange agents, molecular filtration agents, and agents reducing the rate of cholesterol and lipids and/or agents sequestering the biliary acids have already been proposed in the past, cf. to this end French Pat. Nos. 1,363,978 and 1,473,582 and French Patent Applications No. 72-19931 (publication No. 2,140,203) and No. 72-19932 (publication No. 2,140,204). In particular, the above-mentioned French Applications relate to water-and organic solvents-insoluble products but which swell in water and said organic solvents in a gelled form, these swelling products being obtained by copolymerisation of a polyamine, hexamethylenediamine or xylylenediamine, with a bifunctional compound, particularly of the epichlorhydrin or 1,3-glyceroldiglycide-ether type.

According to the invention, a different technical solution is recommended for solving the problem of obtaining a macromolecular substance of three-dimensional structure and capable of swelling in the presence of water and other solvents. In addition, this technical solution has the particular advantage, over the prior art and in particular over the above-mentioned French Applications, of a better swelling power.

The process of preparation according to the invention of a polymer of three-dimensional structure, of the cross-linked polurethane type, and having a good swelling power, is characterised in that
(1) the following are reacted:
 (a) a polyolether, chosen from the group constituted by the oxyalkylene polyols (I) and mixtures thereof obtained by condensation of a polyol (II) containing at least two OH groups and preferably 3 to 6 OH groups with an alkylene oxide (III) at a rate of 1 to 20 moles of (III) per free OH group of (II), and
 (b) a polyisocyanate (IV),
the reaction being carried out with an excess of OH groups of (I) with respect to the NCO isocyanate groups of (IV) to obtain a polyurethane-polyol (V) having free OH groups; and
(2) the polyurethane -polyol (V) thus obtained is reacted with epichlorhydrin (VI) and a polyamine (VII) chosen from the polyamines having at least two $NH_2$ amino groups and mixtures thereof.

From suitable polyolethers, mention may be made of those obtained by reaction (i) of a polyol such as sorbitol, dulcitol, pentaerythritol, the alkyleneglycols, particularly ethylene glycol and propylene glycol, and, in general, triols, tetraols, pentols, hexols, and mixtures thereof, with (ii) an alkylene oxide (shortened to AO), particularly ethylene oxide and propylene oxide, at a rate of 1 to 20 AO groups per free OH of (II).

From suitable polyisocyanates (IV) according to the invention, particular mention may be made of the substances containing at least 2 free NCO groups, mixtures thereof and their prepolymers with the polyols, said prepolymers containing at least 2 free NCO groups per molecule. Among the polyisocyanates which may be used, the most advantageous are 2,4-toluene-diisocyanate, 2,6-toluene-diisocyanate, diphenylmethyl-diisocyanate, the preferred polyisocyanates being 2,4-toluenediisocyanate and commercial toluenediisocyanate containing 80% by weight of 2,4-isomer and 20% by weight of 2,6-isomer.

The reaction of stage (1) is carried out at a temperature of between 20° and 150° C., preferably at a temperature of between 100° and 140° C., for at least 1 hour and preferably for 2 to 3 hours, in a nitrogen atmosphere. The quantities of (I) and of (IV) to be preferably used at stage (1) are such that the ratio [NCO]-[OH], where [NCO] represents the total number of free NCO groups coming from (IV) and [OH] the total number of free OH groups coming from (I), is between (1:3) and (3:4), this ratio being more preferably comprised between (1:2) and (2:3).

In the following specification, the compounds (V) obtained from a ratio (1:3) or (3:4) as defined hereinabove, will be called polyurethane-polyol (1:3) and polyurethane-polyol (3:4) respectively.

At the end of stage (1) and before stage (2) is carried out, the polyurethane-polyol (V) is made to swell by means of a solvent chosen particularly from water and the conventional organic solvents such as acetone, tetrahydrofuran, dimethylformamide, halogenated solvents, particularly dichloroethane, chloroform, carbon tetrachloride and mixtures thereof. Dichloroethane, dimethylformamide or water will preferably be used, and more advantageously dimethylformamide will be used.

Swelling is carried out so that the polyurethanepolyol (V) has a volume 2 to 20 times, and preferably 5 to 10 times, its initial volume. Swelling is effected with stirring. After the swelling has reached the desired volume, the polyurethane-polyol thus swelled is crushed into particles which are as fine as possible, then dried, and the swelling solvent is eliminated.

Without departing from the scope of the invention, the epichlorohydrin which is the preferred means of stage (2), may be replaced by an equivalent means, such as for example epibromhydrin halohydrins and, in general, the bifunctional compounds described in the above-mentioned French Applications.

From the polyamines (VII) which may be used in stage (2), particular mention may be made of aliphatic diamines, aromatic diamines, and aralkylic diamines, particularly hexamethylenediamine, phenylenediamine and xylylenediamine, the preferred diamine being hexamethylenediamine. The $-NH_2$ amino groups of means (VII) may, if necessary, be quaternised into $-NH_3^{+-}$ groups.

The reaction of stage (2) will advantageously be carried out by using a ratio of number of free OH groups of (V) to number of epoxide groups of epichlorohydrin of between (1:1) and (1:50) as well as a ratio of number of free OH groups of (V) to number of $NH_2$ amino groups of (VII) of between (1:1) and (1:50).

In stage (2), either the epichlorhydrin is reacted before the polyamine, or the polyamine before the epichlorhydrin, or these two means at the same time. From the practical point of view, it is recommended to carry out the epichlorohydrin before the polyamine.

The reaction of stage (2) is (i) effected at a temperature of between 20° and 100° C. (advantageously between 40° and 80° C. and preferably 60°-70° C.) for 2 minutes to 2 hours, with stirring, until the reaction medium gels, then (ii) continued, stirring no longer being necessary, at a temperature of 60°-70° C. for 4 to 8 hours, until the compounds (VI) and (VII) have disappeared from the reaction medium.

Stage (2) is carried out in the presence of a solvent chosen from water, conventional organic solvents such as acetone, dimethylformamide, tetrahydrofuran, halogenated solvents, particularly dichloroethane, chloroform, carbon tetrachloride and mixtures thereof. The preferred solvents are dichloroethane and water.

The product thus obtained is subjected to suction then dried at 40°-80° C. (preferably at 50° C.) for 24 to 72 hours (and preferably 48 hours). Drying may be effected at atmospheric pressure or in vacuo.

The water absorption tests were carried out with the aid of an experimental device for rapidly measuring the absorption as a function of time, and shown schematically in FIG. 1 hereinafter. This device comprises a filter crucible 1 (of the crucible for filtration type made of fritted glass No. 3), having an inner diameter 2 of 20 mm and placed in a tank 3 filled with distilled water 4, the top part of the fritted glass 5 being located 1 cm below the level 6 of the water. Under these conditions, the filter crucible is subjected from beneath to a water pressure of 1 g/cm$^2$ sufficient to provoke seeping through the fritted glass. 0.5 g of powdered polymer to be studied is placed in contact with the whole of the moist wall 5. The quantity of water absorbed is measured by weighing the whole (filter, polymer, absorbed water) every 10 seconds.

Figure 2:
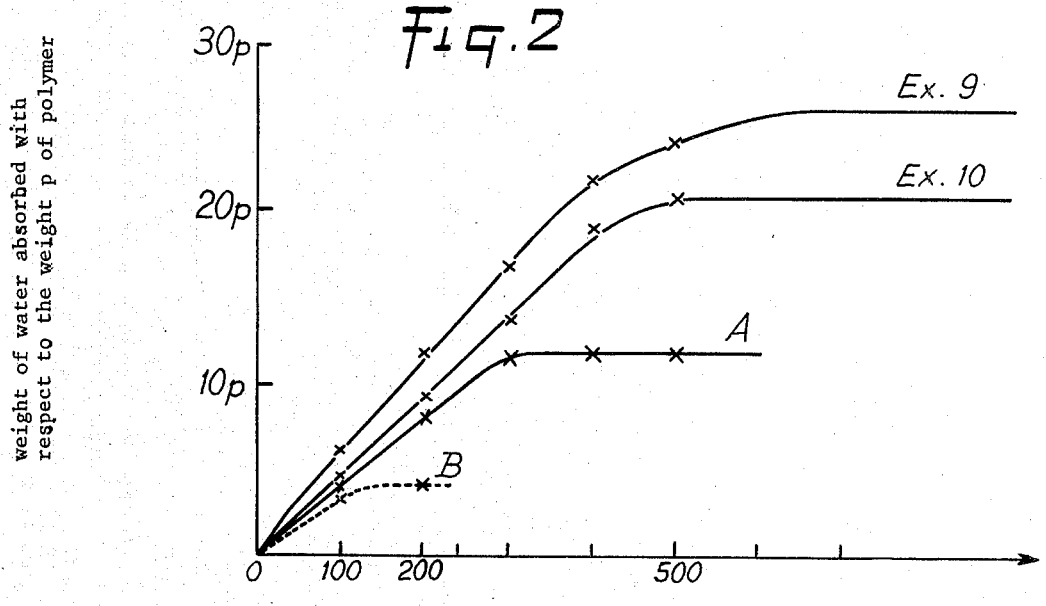

FIG. 2 illustrates the results obtained according to this technique for the products of examples 9 and 10, the product of comparative example A, and a reference product B marketed as swelling agent under the name of Debrisan. In FIG. 2 the weight of water absorbed with respect to the weight p of the polymer is a function the time given in seconds.

The expression "hydrophilic power" will be used hereinafter for convenience to designate the maximum value of the quantity of water absorbed by weight with respect to the weight of the polymer.

The plasmophilic power is determined according to the technique set forth hereinabove for the hydrophilic power.

The polymer obtained according to the process of the invention has a hydrophilic power of 1500 to 4000% by weight (15 to 40 times its weight of water) and has a plasmophilic power of 1200 to 2500% by weight (12 to 25 times its weight of plasma), whilst the products of the comparative examples have a hydrophilic power of 1100% by weight (product A) and 500% by weight (product Abis), and the reference product B has a hydrophilic power of 400 to 600% (on average 500%) according to the technique described hereinabove.

The polymer according to the invention is heat-stable. It is not degraded at a temperature which may reach up to 200° C. or more. In particular, it is not degraded by an exposure to 150° C. for 1 hour. It is sterilisable by heat, by UV as well as by ethylene oxide vapour.

The polymer according to the invention may be presented in the form of gel, powder, balls or crystals.

The polymer according to the invention, crushed in water, gives a particulate gel having thixotropic properties. In this form, it may be used as skin hydrating agent. The gel may also be used in a thin layer as make-up base and to attenuate wrinkles. This gel may also be used in the field of dressing, in the case of swellings of inflammatory nature, or when it is desired for example to reduce the local bodily temperature (for example by winding the dressing including said gel around the calves).

The polymer in the form of powder, balls or crystals may be used directly on the wounds, may be administered by the oral route (agent sequestering biliary acids and/or anorexiant agent), or may be used as ion exchange substance.

The best embodiment of the invention will be described hereinafter.

In stage (1) a polyolether I (which was previously dehydrated at 120° C. in vacuo for 3 hours and which has an equivalent molecular weight of 100 to 160 and an OH index of 475 to 505) is condensed with a polyisocyanate IV (preferably 2,4-toluene-diisocyanate or commercial toluenediisocyanate containing 80% by weight of 2,4-isomer and 20% by weight of 2,6-isomer), at a temperature of 100°-140° C., for 2-3 hours, in a nitrogen atmosphere, in the presence of an excess of free OH groups coming from I with respect to the free NCO groups coming from IV, at a rate comprised between 1 NCO group for 3 OH groups to obtain a polyurethane-polyol (1:3), and 3 NCO groups for 4 OH groups, to obtain a polyurethane-polyol (3:4), the most interesting products being the polyurethane-polyols (1:2)–(2:3).

The polyurethane-polyol V thus obtained is then swelled by means of dimethylformamide, so that the polymer has a volume of 2 to 20 times, and preferably 5 to 10 times, its initial volume. After swelling, the polyurethane-polyol is crushed, then dried at 50° C. and the dimethylformamide is eliminated.

In stage (2), the polyurethane-polyol V (1 to 20 parts by weight) is reacted in a solvent (water or dichloroethane) with epichlorhydrin (30 to 60 parts by weight) and polyamine (40 to 100 parts by weight) - the preferred polyamine being hexamethylenediamine, the preferred quantities of polyurethane-polyol-epichlorhydrin-hexamethylenediamine being (1:3:6) parts by weight to (1:6.6:10) parts by weight-, at a temperature of 60°-70° C., with stirring, until the reaction medium sets (20-60 mins), then, after setting, at a temperature of 60°-70° C. for 4 to 8 hours without it being necessary to stir, the polyamine being used in the form of free base or in the form of hydrochloride (obtained in particular by salification of the free base with 10N HCl, up to pH 1-3). The expected polymer is collected by dewatering (with suction), oven-drying at 50° C. for 48 hours, with a yield of between 60 and 80%.

The product obtained according to the best embodiment from a polyurethane-polyol (1:2)–(2:3) is a crystalline substance, melting at about 240° C. and having a density of 1.1 g/cm$^2$. After use, this substance may be regenerated by dewatering and oven-drying, as indicated hereinabove, then sterilised. (pellet obtained by intimately mixing the polymer to be studied with KBr then compressing) of HP 102 and of the reference product B demonstrates several structural differences. The characteristic peaks are shown in Table I. The IR spectrum of HP102 is given in FIG. 3 (percentage of transmission with respect $\nu$ in $cm^{-1}$).

TABLE I

| Product | NMR | IR | Remarks |
|---|---|---|---|
| HP 102 (Example 5) | 8–10 ppm ≅3 ppm | 800 cm$^{-1}$ 3000–3200 cm$^{-1}$ 1200–1250 cm$^{-1}$ | aromatic cycle OH bond C—O bond (epoxide) absence of C=O bond |
| B | | | absence of aromatic cycle at 8–10 ppm and 800 cm$^{-1}$ |
| | 3.5 ppm 4.3 ppm 0.6–1 ppm | | other differences with HP 102 |

The invention will be more readily understood on reading the following examples of preparation given by way of non-limiting illustration.

EXAMPLE 1

(1) 100 g of polyolpolyether (having an equivalent molecular weight of 100 to 160 and an OH index of 475 to 505 and resulting from the reaction of condensation of sorbitol with propylene oxide) are dehydrated at 120° C. in vacuo for 3 hrs, then 40 g of toluenediisocyanate (mixture of 80% by weight of 2,4-isomer and of 20% by weight of 2,6-isomer) are reacted between 100° and 140° C. for 1 to 3 hours. 130 g of solid polyurethane-polyol (1:2) are obtained which are left to stand for 12 hours at 15°–25° C. This polyurethane is then swelled by means of dimethylformamide up to 10 times its volume, then it is crushed into the finest possible particles. These particles are dried, washed with water, filtered, contracted in the sufficient volume of alcohol (CH$_3$OH or C$_2$H$_5$OH), filtered again, contracted in water, then washed in water until the alcohol and the swelling solvent (DMF) are eliminated.

(2) 50 g of polyurethane thus treated are reacted in water, at 70° C., with 200 g of epichlorhydrin, then 300 g of hexamethylenediamine, the duration of setting being 20 mins., the reaction being continued after setting for 4 hours at 70° C. A consistent gel is obtained which becomes crystalline with stirring in the swollen state. Dewatering is effected then drying at 50° C. for 48 hours in an oven, at atmospheric pressure.

Absorbent power (on average): water: 2800% (28 times its weight of water); plasma: 1800% (18 times its weight in plasma)

density: 1.1 g/cm$^3$
melting point: 240° C.
yield: 60%

EXAMPLE 2

50 g of polyurethane-polyol (1:2) obtained according to stage 1 of Example 1, are swelled in a minimum of distilled water, 300 g of hexamethylenediamine dissolved in 200 ml of distilled water are then added. The mixture is stirred and is heated to 70° C., after 10 mins., 200 g of epichlorohydrin are added. Setting occurs after 1 hour, stirring is then stopped and heating is continued for 4 hours, 10N HCl is then added up to pH 2–3. The product is then washed in water, the gel obtained agglomerates and the particles adhere weakly to one another. The product is contracted with 96% ethanol, dewatered and over-dried under atmospheric pressure for 48 hours at 50° C.

yield: 60%

Hydrophilic power: 18 to 24 times its weight (20 times on average)

EXAMPLE 3

In a reactor provided with stirring means, 50 g of polyurethane-polyol (1:2) prepared according to stage 1) of Example 1 and 100 ml of dichloroethane are mixed, 300 g of hexamethylenediamine are added, then 200 g of epichlorhydrin are introduced drop by drop for 20 mins. at 70° C.; the reaction medium having set, stirring is continued for 8 hours. The mixture is then acidified with 10 N hydrochloric acid, up to pH 1. The product is washed with distilled water up to pH 7. After contraction with ethanol, the product obtained is oven-dried at 50° C. for 48 hrs.

Yield: 80%

Hydrophilic power: 26 to 32 times its weight (28 times on average).

EXAMPLE 4

In a reaction vessel provided with stirring means, 50 g of polyurethane-polyol (1:2) prepared according to stage 1) of Example 1 are mixed with the minimum of distilled water, and 150 g of epichlorhydrin are introduced. 300 g of hexamethylenediamine are then added, with stirring, at 70° C. Setting occurs after 20 mins.

Reaction is continued for 4 hours. The mixture is then acidified to pH 1 with 10 N HCl. The product is washed in water up to pH 7. After contraction in ethanol, the product is dried at 50° C. for 48 hours.

Yield: 60%

Hydrophilic power: 18 to 24 times its weight (20 times on average).

EXAMPLE 5

(Coded as "HP 102")

(1) 100 g of polyolpolyether (previously dried at 120° C. in vacuo for 3 hours, having a mean molecular weight of 702, and equivalent molecular weight of 117 and an OH index of 475–505, prepared from sorbitol and propylene oxide and marketed under the name "UGIPOL 3540") are condensed at 100°–140° C., for 2 hours, with stirring and in an atmosphere of nitrogen, with 37 g of toluenediisocyanate (having a molecular weight of 174 and an equivalent molecular weight of 87, and marketed under the name "LILENE T 80"). The polyurethane-polyol (1:2) thus obtained is swollen in dimethylformamide up to ten times its initial volume, then is crushed, washed in water, contracted in the minimum volume of C$_2$H$_5$OH, filtered, contracted in water, then washed with water.

(2) 30 g of the polyurethane-polyol (1:2) thus obtained are reacted in water with 200 g of epichlorhydrin and 300 g of hexamethylenediamine, this latter substance being introduced drop by drop into the reaction medium constituted by the other ingredients. The reaction is carried out at 70° C. for 40 mins. with stirring until setting occurs, then is continued with stirring for 4 hours at 70° C. 10 N HCl is added until the pH is 2–3, the mixture is washed with water up to pH 7, dewatered, then dried at 50° C. for 48 hours under atmospheric pressure.

Yield: 80%

Hydrophilic power: 26 to 32 times its weight (28 times on average)

Melting point: 240° C.

Figure 3:
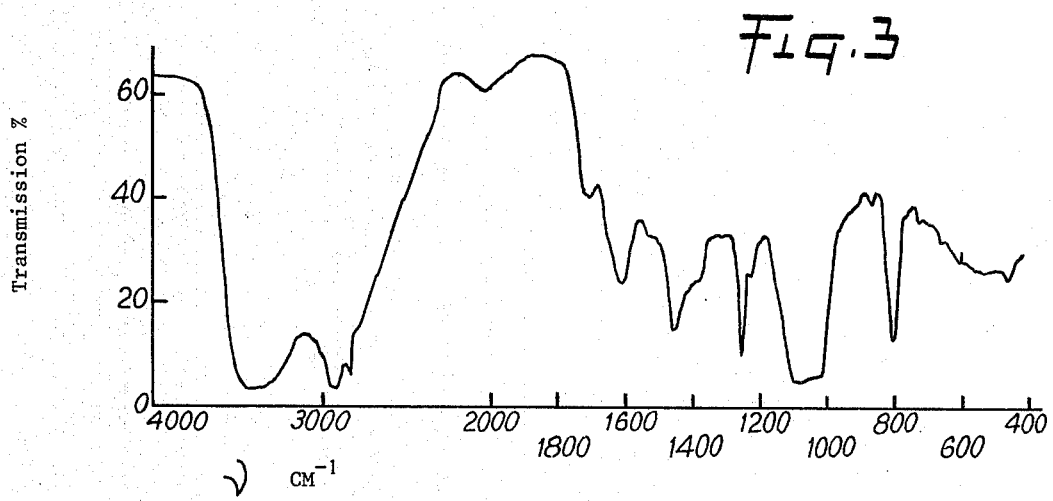

IR spectrum: cf. FIG. 3

EXAMPLE 5 bis

By proceeding as indicated in Example 5 and replacing the respective proportions of polyurethane-polyol (1:2)-epichlorhydrin-hexamethylenediamine which ae (1:6.6:10) parts by weight, by the proportions (1:6.6:9) parts by weight, the same polymer is obtained with a yield of 80%.

Following Example 6 illustrates the obtaining of a polymer according to the invention, from a small quantity of polyurethanepolyol with respect to the quantities of epichlorhydrin and hexamethylenediamine.

EXAMPLE 6

5 g of polyurethane-polyol (1:2) prepared according to stage 1) of Example 5 and 180 g of epichlorohydrin are dissolved in 800 ml of distilled water, with stirring, at 70° C. After 10 mins., 220 g of hexamethylenediamine in 50 ml of water are added. The setting time is 40 mins; reaction is continued at 70° C. for 4 hrs. Acidification to pH 1 is made with 10 N HCl. The product is mixed twice in water and contracted with ethanol; the product is then dried at 50° C. for 48 hours in an oven under atmospheric pressure.

Yield: 60%

Hydrophilic power: 16 to 18 times its weight (17 times on average)

Following Example 7 illustrates the obtaining of a polymer according to the invention from a large quantity of polyurethane-polyol with respect to those of epichlorhydrin and hexamethylenediamine.

EXAMPLE 7

In a reactor provided with a stirring means, 100 g of polyurethane-polyol (1:2), prepared according to stage 1 of Example 5, are mixed in a minimum quantity of distilled water with 180 g of epichlorhydrin 270 g of hexamethylenediamine in 500 ml of water are then added. The mixture is stirred and is heated to 70° C. for 1 hour up to setting. The reaction is continued for 4 hrs. at 70° C., 10 ml of 10 N hydrochloric acid are added in the mixture. The product is mixed twice in water, it is contracted in ethanol and dried at 50° C. for 48 hours.

Yield: 60%

Hydrophilic power: 18–22 times its weight (20 times on average)

EXAMPLE 8

30 g of polyurethane-polyol (1:2), prepared according to stage 1 of Example 5, 180 g of epichlorhydrin in 800 ml of distilled water are mixed; after 10 mins. of stirring, 200 g of hexamethylenediamine dissolved in 500 ml of water are added. Setting occurs after 40 mins. at 70° C., with stirring. The reaction is continued for 4 hours at 70° C. The product is acidified to pH 1 with 10 N hydrochloric acid, washed in water, contracted with ethanol and oven-dried at 50° for 48 hours.

Yield: 60%

Hydrophilic power:24 to 30 times its weight (26 times on average).

EXAMPLE 9

In a reactor provided with stirring means, 30 g of polyurethane-polyol (2:3), prepared as indicated in Example 5 from polyolpolyether and toluene diisocyanate at a rate of 2 NCO groups for 3 OH groups, in 800 ml of water are mixed with 180 g of epichlorhydrin. After 10 mins. of stirring, 200 g of hexamethylenediamine dissolved in 500 ml of water are added. Setting occurs after 40 mins. at 70° C., with stirring.

Reaction is continued for 4 hrs. at 70° C. The product is acidified, washed, contracted in ethanol and dried at 50° C. for 48 hrs.

Yield: 60%

Hydrophilic power: 22 to 28 times its weight (26 times on average)

EXAMPLE 10

In a flask provided with stirring means are mixed 30 g of polyurethane-polyol (2:3) obtained as indicated in Example 9 and swollen in 500 ml of dichloro-ethane, and 180 g epichlorhydrin. After 10 mins. of stirring at 60° C., 200 g of hexamethylenediamine dissolved in 500 ml of water are added. Setting occurs after 20 mins. Reaction is then continued for 8 hours at 60° C. The product obtained is acidified, washed, contracted and dried at 50° C. for 48 hours.

Yield: 80%

Hydrophilic power: 20 to 26 times its weight (24 times on average)

EXAMPLE A (comparative)

270 g of hexamethylenediamine and 600 ml of water are mixed in a reactor provided with a stirring means. 200 g of epichlorhydrin are added drop by drop in 500 ml of dichloroethane. The mixture is heated to 60° C., with stirring, for 20 mins., then without stirring for 8 hours. The gel formed is acidified with 10 N hydrochloric acid up to pH 1. The product is washed in distilled water up to pH 7, contracted with 96% ethanol and oven-dried at 50° C. for 48 hours.

Yield: 80%

Hydrophilic power: 10 to 12 times its weight (11 times on average).

EXAMPLE ABIS (comparative)

In a flask provided with stirring means are mixed 30 g of polyurethane-polyol (1:2), prepared according to stage (1) of Example 1, and swollen in 500 ml of dichloroethane, and 180 g of epichlorhydrin. After 10 mins. of stirring at 60° C., 200 g of carbailide dissolved in 500 ml of water are added. Setting occurs after 60 mins., then the reaction is continued for 4 hours at 60° C. The product obtained is acidified, washed, contracted and dried at 50° C. for 48 hours.

Yield: 25%

Hydrophilic power: 4 to 6 times its weight (5 times on average).

EXAMPLE ATER

When the polyurethane-polyol V is reacted with hexamethylenediamine in water at 60°–70° C., with stirring (without using epichlorhydrin), a sparingly hydrophilic, but sticky elastomer is obtained.

EXAMPLE 11

The procedure is as indicated in Example 1 to obtain a polyurethane-polyol (1:3) by dehydration at 100° C. in vacuo for 3 hours of 100 g of polyol-polyether then reaction with 25 g of toluenediisocyanate.

In the polyurethane-polyol (1:3) thus obtained are introduced the epichlorhydrin and the hexamethylenediamine as in stage 2 of Example 1.

EXAMPLE 12

A polyurethane-polyol (3:4) is prepared as indicated in Example 1 by reacting, in stage 1, 100 g of polyol-polyether with 60 g of toluene diisocyanate. The procedure is then as indicated in stage 2 of Example 1.

The modi operandi of stage (2) for obtaining the polymers of the preceding examples are summarised in Table II hereinbelow with the swelling powers of said examples.

The polymer obtained according to the process of the invention, and more precisely the one of examples 1–12, is in the form of powder in the crystallised state, the particles having a diameter of between 5 and 50μ (10μ on average).

TABLE II

| Example | 1 | 2 | 3 | 4 | 5 | 6 |
|---|---|---|---|---|---|---|
| Polyurethane-polyol V | (1:2) | (1:2) | (1:2) | (1:2) | (1:2) | (1:2) |
| Solvent | water | water | dichloro-ethane | water | water | water |
| Mode of introduction of reagents | (a) | (b) | (b) | (a) | (a) | (a) |
| Respective quantities (d) | 1:4:6 | 1:4:6 | 1:4:6 | 1:3:6 | 1:6.6:10 | 1:36:44 |
| Duration of reaction  setting | 20 mins | 60 mins | 20 mins | 40 mins | 40 mins | 40 mins |
| after setting | 4 hrs | 4 hrs | 8 hrs | 4 hrs | 4 hrs | 4 hrs |
| Reaction temperature | 70° C. | 70° C. | 60° C. | 70° C. | 70° C. | 70° C. |
| Drying  duration | 48 hrs | 48 hrs | 48 hrs | 48 hrs | 48 hrs | 48 hrs |
| temperature | 50° C. | 50° C. | 50° C. | 50° C. | 50° C. | 50° C. |
| Yield | 60% | 60% | 80% | 60% | 80% | 60% |
| Hydrophilic power (e) (average) | 26p–32p (28p) | 18p–24p (20p) | 26p–32p (28p) | 18p–24p (20p) | 26p–32p (28p) | 16p–18p (17p) |

| Example | 7 | 8 | 9 | 10 | A | Abis |
|---|---|---|---|---|---|---|
| Polyurethane-polyol V | (1:2) | (1:2) | (2:3) | (2:3) | — | (1:2) |
| Solvent | water | water | water | dichloro-ethane | dichloro-ethane | dichloro-ethane |
| Mode of introduction of reagents | (a) | (a) | (a) | (a) | (b) | (c) |
| Respective quantities (d) | 1:1.8:2.7 | 1:6:6.6 | 1:6:6.6 | 1:6:6.6 | VI–VII = 1:1.35 | 1:6:6.6 |
| Duration of reaction  setting | 60 mins | 40 mins | 40 mins | 20 mins | 20 mins | 60 mins |
| after setting | 4 hrs | 4 hrs | 4 hrs | 8 hrs | 8 hrs | 4 hrs |
| Reaction temperature | 70° C. | 70° C. | 70° C. | 60° C. | 60° C. | 60° C. |
| Drying  duration | 48 hrs | 48 hrs | 48 hrs | 48 hrs | 48 hrs | 48 hrs |
| temperature | 50° C. | 50° C. | 50° C. | 50° C. | 50° C. | 50° C. |
| Yield | 60% | 60% | 60% | 80% | 80% | 25% |
| Hydrophilic power (e) (average) | 18p–22p (20p) | 24p–30p (28p) | 22p–28p (26p) | 20p–26p (24p) | 10p–12p (11p) | 4p–6p (5p) |

Notes:
(a): epichlorhydrin before hexamethylenediamine
(b): hexamethylene diamine before epichlorhydrin
(c): epichlorhydrin before carbailide ($C_6H_5NHCONHC_6H_5$)
(d): respective quantities in parts by weight of polyurethane-polyol-epichlorhydrin -hexamethylenediamine for Ex. 1–10 epichlorhydrin -hexamethylenediamine for Example A, and polyurethane-polyol-epichlorhydrin -carbailide for Example Abis
(e): expressed by weight with respect to the weight p of the polymer obtained after drying of stage (2).

The pharmacological and clinical tests which were carried out have demonstrated that the polymer according to the invention is not very toxic, particularly by the oral route, and that it is useful in therapeutics (treatment of wounds to absorb the bodily fluids, sequestration of biliary acids, appetite-reducing action due to swelling thereof in the stomach) and in cosmetics.

The polymer according to the invention in the form of powder (particularly in the form of spherical or crystalline particles) may be simultaneously projected with fibres onto a transfer support paper coated with silicone) or on a final support (non-stick tulle, biogauze or crepe). The assembly obtained is a composite product, the particles of polymer and the fibres constituting a non-woven fabric which may be used in dressings, said non-woven fabric facilitating the application and removal of the polymer from the wound.

Figure 4:
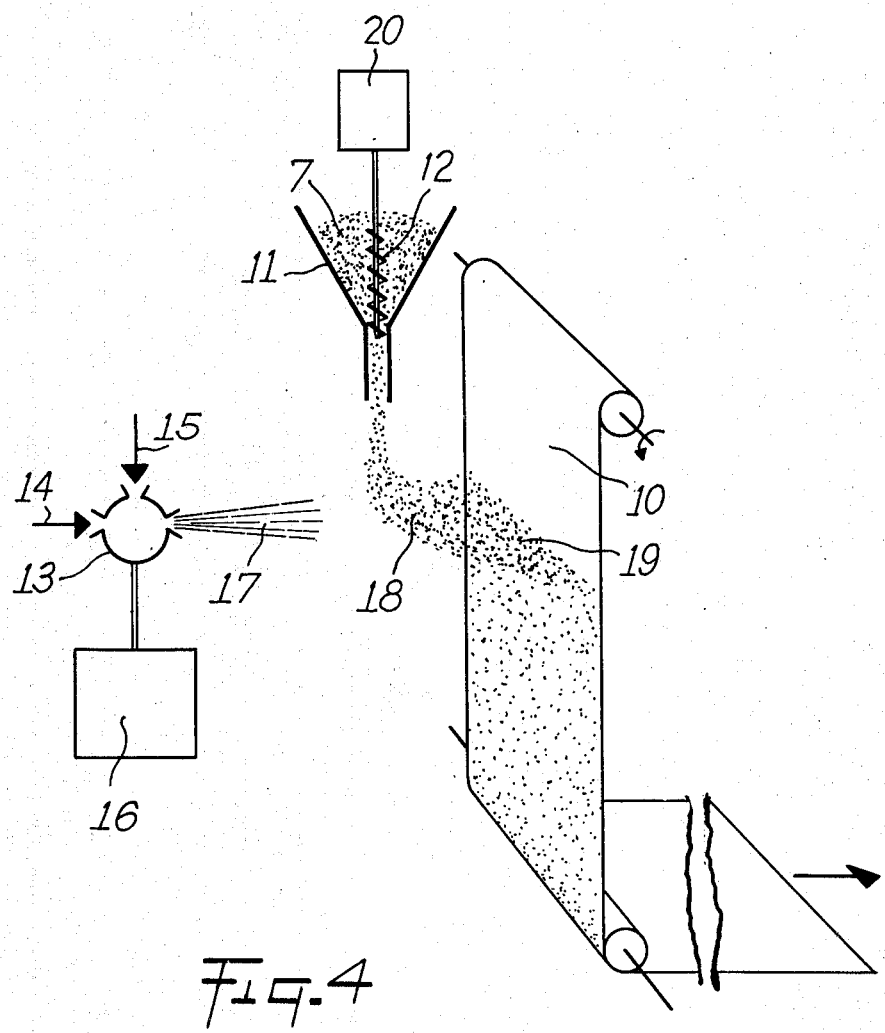

FIG. 4 schematically shows the mode of obtaining the non-woven fabric constituted by the polymer according to the invention and the fibres. The powdered polymer 7, which comes from a hopper 11 comprising a distributing screw 12 driven by a motor 20 gives a flow 18 entrained towards the support 10 (preferably a transfer support made of paper coated with silicone) by a flow 17 coming from a projecting device 13 driven by a motor 16 and receiving compressed air 14 and an elastomer [butadiene-styrene (50:50) by weight copolymer] in solution in a solvent (particularly ethyl acetate) which is introduced at 15. During projection by means of the compressed air 14, the elastomer is dried and gives fibres conveyed by the flow 17.

Together, the flows 17 and 18 allow the deposit at 19 on the support 10, as the latter moves, of fibres and polymer according to the invention.

The polymer in powder form may also be packed according to the invention in a non-stick, porous sachet (particularly woven or non-woven) for making dressings.

The polymer in powder form according to the invention may also be used as swelling agent for incorporation in babies' napkins and draw-sheets for the elderly and incontinent subjects. In this type of application, the swelling agent may be packed dry in liquid-permeable bags disposed in said napkins and draw-sheets.

The polymer in powder form according to the invention may also be used in the swollen state (with water) and packed in one or more porous bags as saturator, particularly for radiators.

Finally, it has been observed that the polymer according to the invention presents antiseptic properties beneficial in therapeutics and in cosmetics.

What is claimed is:

1. A process for preparing a polymer having a three-dimensional structure of the cross-linked polyurethane type and having a good swelling powder, said process comprising the following steps of:
   (1) reacting
      (a) a polyether, selected from the group consisting of the oxyalkylene polyols (I) and mixtures thereof, obtained by condensation of a polyol (II) containing at least 2 OH groups with an alkylene oxide (III) at a rate of 1 to 20 moles of (III) per free OH group of (II), with
      (b) a polyisocyanate (IV),
   the reaction being carried out with an excess of OH groups of (I) with respect to the NCO isocyanate groups of (IV) to obtain a polyurethane-polyol (V) having free OH groups; and
   (2) reacting the resulting polyurethane-polyol (V) with epichlorhydrin (VI) and a polyamine (VII) selected from the group consisting of polyamines having at least two $NH_2$ amino groups and mixtures thereof.

2. The process of claim 1, wherein the polyolether of step (1) is obtained from a polyol selected from the group consisting of alkylene glycols, triols, tetraols, pentols, hexols and mixtures thereof.

3. The process of claim 1, wherein the polyisocyanate used in step (1) contains at least 2 free NCO groups per molecule.

4. The process of claim 3, wherein the polyisocyanate is selected from the group consisting of toluenediisocyanate, 2,6-toluenediisocyanate, diphenylmethyldiisocyanate and mixtures thereof.

5. The process of claim 3, wherein the polyisocyanate is selected from the group consisting of 2,4-toluenediisocyanate and an (80:20) by weight mixture of 2,4-toluenediisocyanate and 2,6-toluenediisocyanate.

6. The process of claim 1, wherein the reaction of step (1) is carried out at a temperature between 20° and 150° C. for at least one hour in a nitrogen atmosphere.

7. The process of claim 1, wherein the reaction of step (1) is carried out with respective quantities of polyolether I and of polyisocyanate IV such that the weight ratio of the number of free NCO groups coming from IV to the number of free OH groups coming from I is between (1:3) and (3:4).

8. The process of claim 1, wherein, after step (1) but before step (2), the obtained polyurethane-polyol V is subjected to swelling by means of a substance selected from the group consisting of water, organic solvents and mixtures thereof.

9. The process of claim 8, wherein the swelling is carried out in such a manner that the swollen polyurethanepolyol V has a volume of 2 to 20 times its initial volume.

10. The process of claim 1, wherein the reaction of step (2) is (i) carried out at a temperature of between 20° and 100° C. for 2 minutes to 2 hours, with stirring, until the reaction medium gels, then (ii) continued, stirring no longer being necessary, at a temperature between 60° and 70° C. for 4 to 8 hours, until the epichlorhydrin and polyamine have disappeared from the reaction medium.

11. The process of claim 1, wherein the polyamine of step (2) is selected from the group consisting of aliphatic, aromatic and aralkylic diamines.

12. The process of claim 1, wherein the reaction of step (2) is carried out in the presence of a solvent selected from the group consisting of water, acetone, dimethylformamide, tetrahydrofuran, dichloroethane, chloroform, carbon tetrachloride, and mixtures thereof.

13. The process of any one of claims 10, 11 or 12, wherein the product obtained in step (2) is subjected to dewatering in vacuo and then dried at 40° to 80° C. for 24 to 72 hours.

14. A process according to claim 1, comprising the steps of:
   condensing a polyolether I previously dehydrated at 120° C. in vacuo for 3 hours and having an equivalent molecular weight of 100 to 160 and an OH index of 475 to 505 with a polyisocyanate IV at a temperature of 100° to 140° C., for 2 to 3 hours, in a nitrogen atmosphere, in the presence of an excess of free OH groups coming from I with respect to the free NCO groups coming from IV, at a ratio between 1 NCO group for 3 OH groups (1:3) and 3 NCO groups for 4 OH groups (3:4) to obtain a polyurethane-polyol;
   swelling the resulting polyurethane-polyol V by means of dimethylformamide so that the polymer has a volume of 2 to 20 times its initial volume;
   crushing the swollen polyurethane-polyol and drying the crushed material at 50° C. to eliminate the dimethylformamide;
   reacting in a solvent selected from the group consisting of water and dichloroethane, 1 to 20 parts by weight of polyurethane-polyol V with 30 to 60 parts by weight of epichlorhydrin and 40 to 100 parts by weight of polyamine at a temperature of 60° to 70° C. with stirring for 20 to 60 minutes until the reaction medium sets, then at a temperature of 60° to 70° C. for 4 to 8 hours, the polyamine being used in the form of free base or hydrochloride; and
   collecting the resulting polymer by dewatering then drying at 50° C. for 48 hours.

15. The process of claim 14, wherein the diamine is hexamethylenediamine and the quantities of polyurethane-polyol, epichlorhydrin and hexamethylenediamine are in a weight ratio from (1:3:6) to (1:6:6:10).

16. A polymer having a three-dimensional structure of the cross-linked polyurethane type and having a good swelling power prepared in accordance with any one of claims 1 to 14.

17. A polymer having a three-dimensional structure of the cross-linked polyurethane type and having a good swelling power, a density of 1.1 g/cm$^3$, a crystalline form and a melting point of 240° C., and exhibiting NMR peaks at 8–10 ppm and 3 ppm and IR peaks at 800 cm$^{-1}$, 3000–3200cm$^{-1}$ and 1200–1250 cm$^{-2}$.

18. The polymer of claim 17, having a swelling power with respect to water, from 1500 to 4000% by weight, and, with respect to plasma, from 1200 to 2500% by weight.

19. The polymer of claim 18, having a swelling power, with respect to water, from 2600 to 3200% by weight, and comprising a reaction product of polyurethanepolyol V, and hexamethylenediamine in a weight ratio of (1:4:6).

20. A composition useful in therapeutics and cosmetics, containing as active ingredient a polymer according claim 15.

* * * * *